(12) United States Patent
Barker (10) Patent No.: US 7,118,218 B2
(45) Date of Patent: Oct. 10, 2006

(54) METHOD AND DEVICE FOR IMAGING A SECTION OF THE EYEGROUND

(75) Inventor: Felix Barker, Elkins Park, PA (US)

(73) Assignee: Haag-Streit AG, Koniz (CH)

( * ) Notice: Subject to any disclaimer, the term of this patent is extended or adjusted under 35 U.S.C. 154(b) by 835 days.

(21) Appl. No.: 10/276,403

(22) PCT Filed: Feb. 5, 2001

(86) PCT No.: PCT/CH01/00076

§ 371 (c)(1),
(2), (4) Date: Dec. 18, 2002

(87) PCT Pub. No.: WO01/87146

PCT Pub. Date: Nov. 22, 2001

(65) Prior Publication Data

US 2004/0100618 A1   May 27, 2004

(30) Foreign Application Priority Data

May 17, 2000   (CH)   ..................... 989/00

(51) Int. Cl.
*A61B 3/135* (2006.01)
*A61B 3/13* (2006.01)
*A61B 3/10* (2006.01)
*A61B 3/00* (2006.01)

(52) U.S. Cl. ............... 351/214; 351/200; 351/205; 351/245; 351/246

(58) Field of Classification Search ............ 351/214, 351/245, 246
See application file for complete search history.

(56) References Cited

U.S. PATENT DOCUMENTS 2,622,473 A * 12/1952 Littmann ............. 351/214
2,999,422 A * 9/1961 Papritz ............. 351/214
4,874,236 A * 10/1989 Abraham ............. 351/214

FOREIGN PATENT DOCUMENTS

DE   1 133 911 B   7/1962

OTHER PUBLICATIONS

Barker, Journal of the American Optometric Association, vol. 59, No. 7, pp. 558-560 (1988).

* cited by examiner

Primary Examiner—Charles A. Marmor, II
Assistant Examiner—John Sanders
(74) Attorney, Agent, or Firm—Birch, Stewart, Kolasch & Birch, LLP (57) ABSTRACT

A device for examining for the eyeground of a patient's eye (1) has a head holder (3) for fixing the patient's head and a slit lamp unit (19 or 22). Provided on the head holder is a laterally movable lens carriage (9), in the shaft guide (10) of which a lens holder (11) can be introduced with its shaft (27) from above. For positioning the lens (12) in front of the eye (1), the lens holder is coupled in terms of movement to the microscope by means of an adapter (25) and a guide plate (24). The lens carriage, the lens holder and the adapter or the guide plate are in this case formed in such a way that the lens holder can be spatially fixed and uncoupled from the microscope with few manipulations, which makes it possible for an image of the eyeground to be formed the microscope in an optimum way.

13 Claims, 5 Drawing Sheets

METHOD AND DEVICE FOR IMAGING A SECTION OF THE EYEGROUND

CROSS-REFERENCES TO RELATED APPLICATIONS

This application is a national-stage entry of International Application No. PCT/CH01/00076, filed Feb. 5, 2001, which claims priority from Swiss Application No. 989/00, filed May 17, 2000.

TECHNICAL FIELD

The invention relates to a method and a device, known as a slit lamp unit, for forming an image of a rear portion of a patient's eye, with a viewing unit having a microscope and with an optical unit.

PRIOR ART

The rear portions of an eye, for example the fundus of an eye, are typically examined and an image of them is formed by a slit lamp unit, with what is known as an auxiliary lens being additionally positioned as an optical unit in front of the corresponding eye. Depending on the focal length, this auxiliary lens makes it possible to view regions of different sizes of the eyeground.

To avoid undesired movements of the patient during an examination, the head of the patient is fixed in a head holder. The auxiliary lens is also typically fastened to this head holder. However, in order to permit precise positioning of the auxiliary lens in front of the eye, this connection must be movable.

A holding means for an auxiliary lens of this type is described in Journal of the American Optometric Association, Volume 59, Number 7, 7/88. The holding means comprises a linkage which is connected by joints and is fastened by one end to the head holder and at the other end bears the optical unit. The auxiliary lens must be manually positioned in the desired position in front of the eye, the friction of the joints being sufficient for the auxiliary lens to remain more or less in the set position once it is let go.

However, the problem is that it is only with very great difficulty that the auxiliary lens itself can be manually positioned sufficiently precisely in front of the eye, even by an experienced user. For a layperson, this is virtually impossible.

A further possible way in which an auxiliary lens can be positioned in front of the eye is described in DE 1133911. For this purpose, a lens carriage with a shaft guide, a vertical hole, is fastened to the head holder. The carriage is laterally displaceable, but not vertically displaceable. A matching auxiliary lens has a cylindrical shaft, which can be introduced into the shaft guide on the carriage. As a result, the auxiliary lens is movable both laterally (by displacing the carriage) and vertically (by displacing the shaft in the shaft guide). The holding means for the auxiliary lens itself is movably connected to the shaft, so that the distance of the auxiliary lens from the eye can also be set in the desired way. A screw on the shaft guide allows the auxiliary lens to be fixed in the latter. For easier positioning, the auxiliary lens can also be coupled in terms of movement to the slit lamp unit.

Here, too, it is the case that manual positioning is not sufficiently precise. Moreover, the uncoupling operation is complicated and laborious and the eyeground cannot be scanned with a light slit of a slit lamp unit.

A further problem is that, in the case of known lens holders, although the optical unit is movably connected to the lens holder, it is fixedly connected, i.e. not detachably connected. Therefore, when a lens is changed, the entire lens holder has to be exchanged.

SUMMARY OF THE INVENTION

The object of the invention is to provide a method of the type mentioned at the beginning which avoids the problems existing in the prior art and, in particular, allows precise positioning of the auxiliary lens and also unhindered formation of an image of the rear portion of an eye. Moreover, it is intended that a lens holder which allows the optical unit to be easily exchanged should be provided.

The solution achieving the object is defined in terms of the method by the features of claim 1 and in terms of the device by the features of claim 4. The method according to the invention for forming an image of the rear portions of a patient's eye using a viewing unit and an optical unit comprises at least the following steps:

a) The optical unit is coupled in terms of movement to the viewing unit, having a microscope.

b) The optical unit is positioned in front of the patient's eye in such a way that it is located between the viewing unit and the patient's eye in a given relative position with respect to the patient's eye.

c) The optical unit is spatially fixed in relation to the patient's eye.

d) The optical unit is uncoupled from the viewing unit while maintaining the spatial fixing in relation to the patient's eye.

e) By moving the viewing unit, an image of the rear portion of the patient's eye is formed, the viewing unit moving substantially on a plane perpendicular to the optical axis of the eye and the eyeground being scanned, for example, by a light slit.

The coupling in terms of movement of the optical unit to the microscope of the viewing unit makes it possible to position the optical unit absolutely precisely in front of the eye to be examined by using the viewing unit. The position of the optical unit can be checked at any time by the viewing unit and also corrected by displacing the viewing unit. The spatial fixing and the uncoupling of the optical unit from the viewing unit are performed in an easy and quick way, without the risk of unwanted displacement of the optical unit. Moreover, the auxiliary lens uncoupled according to the invention does not restrict the freedom of movement of the viewing unit, thereby permitting unhindered formation of an image of the rear portions of an eye with the viewing unit. Consequently, all the desired examinations can be carried out on the patient's eye without modifying the slit lamp unit.

To achieve a viewing range which is as extensive as possible, the optical unit is preferably positioned in front of the patient's eye in such a way that its focus or its focal point comes to lie on the plane of the pupil of the patient's eye. In this case, the optical axes of the eye and of the optical unit generally coincide.

For easier and safer handling, the spatial fixing of the optical unit in relation to the patient's eye is preferably performed substantially at the same time as the uncoupling of the optical unit from the viewing unit. It is intended for the fixing and uncoupling to be performed in this case with as few manipulations as possible, advantageously of course with a single manipulation, for example by pressing a button or by actuating a lever.

When forming an image of the rear portions of an eye, the image field is greatly restricted by the relatively small pupillary aperture, for which reason an optical unit is placed between the viewing unit and the eye by coupling said optical unit to the viewing unit. By uncoupling the optical unit after its positioning, a greatly increased image field is achieved when forming the image of the rear portions of the eye.

The device according to the invention for forming an image of the rear portions of an eye, with a viewing unit and an optical unit, comprises means for coupling the optical unit in terms of movement to the viewing unit, means for positioning the optical unit coupled to the viewing unit between the viewing unit and the patient's eye, means for spatially fixing the optical unit in relation to the patient's eye and also means for uncoupling the spatially fixed optical unit from the viewing unit.

For forming an image of the rear portions of an eye, a microscope is preferably used as the viewing unit, for example what is known as a Greenough stereo microscope, as is also used for the examination of eyes. In such examinations, the head of the patient is usually fixed in place. The microscope can then be positioned in any way desired in front of the eye to be examined, more or less freely movably in all directions. What are known as auxiliary lenses, which are usually fastened to a lens holder, are advantageously used as the optical unit.

In the case of a preferred embodiment of the invention, the spatial fixing of the head of the patient (and consequently also of the patient's eye) is performed in a head holder which comprises a lens carriage which is fastened to the head holder in a horizontally movable manner. The horizontal movement of the lens carriage substantially comprises a lateral displacement, so that the lens carriage, and consequently the optical unit, can be placed according to choice in front of the left eye or the right eye of the patient.

A correspondingly formed auxiliary lens is fastened at the upper end of a lens holder to a cylindrical shaft, the shaft being dimensioned in such a way that it can be introduced into a corresponding shaft guide on the lens carriage. The shaft guide comprises, for example, a vertically arranged hole on the lens carriage, into which the shaft of the auxiliary lens can be introduced from above.

For the coupling in terms of movement of the optical unit to the viewing unit, the device has, for example, a guide plate which is fixedly assigned locationally to the viewing unit and has a guide groove. In other words, the guide plate exactly follows the movements of the viewing unit, with the guide groove running horizontally, parallel to the optical axis of the viewing unit, i.e. parallel to the viewing direction of the head of the patient.

The coupling is achieved by the shaft of the lens holder which has been introduced into the shaft guide on the lens carriage being inserted by its lower end into the guide groove. For this purpose, the guide groove and the lower end of the shaft are formed in such a way that the shaft cannot be turned about its longitudinal axis in the guide groove.

The shaft of the lens holder can be inserted into the guide groove not only directly but also indirectly by means of an adapter. For this purpose, the adapter is formed in such a way that it can itself be inserted into the guide groove and the shaft can be inserted into the adapter.

This coupling of the lens holder and viewing unit allows the lateral and vertical movements of the viewing unit to be transferred to the optical unit, with the distance between the optical unit and the eye remaining unchanged. When there are movements of the viewing unit toward the eye or away from the eye, it is merely the shaft that is displaced in the guide groove of the guide plate. The length of the shaft is made to match the microscope, so that the optical axis of the optical unit substantially coincides with the optical axis of the viewing unit, which in the case of a microscope is the axis of symmetry of the two optical axes of the subsystem on the left and the subsystem on the right.

The optical unit is movably connected to the shaft, for example by means of a jointed parallelogram, whereby the frontal distance of the optical unit from the eye can be set in a desired way.

The optical unit can consequently be positioned in any way desired in front of the eye to be examined.

In the case of a preferred embodiment of the invention, the guide plate, the lens holder and the lens carriage are formed in such a way that the optical unit can be spatially fixed in the desired position in front of the patient's eye. The lens holder can be fixed in the shaft guide on the lens carriage and/or the lens carriage can be fixed on the head holder. The fixing is performed, for example, mechanically or magnetically.

A preferred variant for the spatial fixing of the optical unit in relation to the patient's eye is performed mechanically by means of a sleeve attached to the shaft guide of the lens carriage. The shaft of the lens holder is introduced through the sleeve into the shaft guide and firmly clamped in the shaft guide, for example by turning the sleeve in a way known per se, for example by constricting the inside diameter.

Furthermore, the sleeve may have, for example, a ring of external teeth, which puts a gearwheel mechanism into operation when the sleeve is turned, said mechanism activating a brake attached to the lens carriage.

It goes without saying that the lens holder can be fixed in any desired manner. A further possible way is, for example, to provide the shaft of the lens holder with a buckling joint and a spreading mechanism, which is triggered by bending away the lower end. At the same time, the brake on the guide carriage could be activated by means of a lever mechanism.

A further preferred kind of spatial fixing of the optical unit is based on magnetic forces. In this case, the lens holder and/or the lens carriage are firmly clamped in the shaft guide or on the head holder by means of one or more magnets.

In order that the rear portions of the eye can be scanned unhindered with the slit lamp unit, the optical unit is uncoupled from the viewing unit after it has been positioned in front of the eye.

For this purpose, the lens holder, the guide plate and the adapter, if provided, are formed in such a way that the spatially fixed optical unit can be uncoupled from the viewing unit preferably by horizontal and/or vertical moving out or pivoting out of the lower end of the shaft, of the adapter or of the guide plate.

For the uncoupling, the guide plate is, for example, connected to the viewing unit by means of a spring mechanism similar to the refill advancement of a ballpoint pen. The spring mechanism allows the guide plate to be pressed down and in this way releases the shaft of the lens holder by moving out vertically. The spring mechanism is in this case preferably formed in such a way that the guide plate engages in this position and can be released again by pressing once again.

Another variant consists in that the adapter, if provided, has the spring mechanism mentioned above. After pressing down, however, the adapter can be removed manually, for which reason the adapter does not have to engage after the pressing together.

In the case of a further variant, the shaft of the optical unit has, for example, a joint, in particular a buckling joint (as already mentioned further above). The uncoupling of the optical unit from the viewing unit is performed by pivoting the lower end of the shaft out from the guide groove, for example by manual bending of the joint, it being possible, as already described, for the lens holder to be spatially fixed at the same time.

A further possible way of uncoupling the shaft from the guide plate is, for example, to form the lower part of the shaft in such a way that it is telescopically extendable. In other words, the shaft comprises at least two cylindrical parts which can be pushed one into the other. The pushing of one into the other, i.e. the vertical lifting of the lower shaft end out of the guide groove, could be performed, for example, magnetically by activation of a corresponding magnet.

It goes without saying that any desired combinations of mechanical and magnetic fixing and uncoupling of the optical unit are possible.

The positioning of the optical unit in front of the eye can be performed both manually and automatically, in respect of which it goes without saying that mixed forms are also possible. The viewer may, for example, perform rough positioning of the optical unit with the aid of the viewing unit and have the fine adjustment carried out by an automatic positioning device before or after the uncoupling of the optical unit from the viewing unit. Such an automatic positioning device comprises, for example, a pupil sensor for ascertaining the exact position of the pupil of the eye to be examined and also a device for the precise positioning of the optical unit in relation to the pupil. Of course, in addition to the positioning, the uncoupling and fixing of the optical unit may be performed not by the user but by a corresponding automatic device.

In the case of a particularly preferred embodiment of the invention, the uncoupling of the lens arrangement from the viewing unit is performed substantially at the same time as the spatial fixing of the optical unit in relation to the patient's eye, both taking place without any locational displacement of the optical unit. In this case, "substantially at the same time" means that the uncoupling and fixing can be performed by a preferably single movement on the part of the viewer, i.e. by pressing a button or actuating a lever, it being possible for the button or the lever to be attached at a suitable place, for example to the viewing unit, to the head holder or to the optical unit.

For creating images of the portions of an eye to be examined, the viewing unit is preferably formed in such a way that an image acquisition device operates together with it. For example, a video camera or a photo camera may be connected via a corresponding camera adapter. Digital cameras (for example CCD, CMOS) are also very well suited, having the advantage that the images captured can be digitally further processed directly.

Appropriate forming of the camera adapter or the camera also allows further functions to be integrated, such as for example a zoom or fine adjustment. In this way it is possible to select an image cutout of interest and show it enlarged.

To permit easy and quick changing, i.e. exchanging, of the optical unit, the lens holder is formed in such a way that the optical unit can be firmly clamped on the lens holder and removed again manually.

A preferred embodiment of the lens holder comprises two holding parts resiliently connected to each other, which are arranged at a specific distance from each other, corresponding to the thickness of the optical unit. The optical unit can in this way be clamped conveniently and easily between these two holding parts, and similarly be removed again easily.

However, the use of such a lens holder is not restricted to the application in conjunction with the device described above. It goes without saying that it can be used wherever optical units, for example individual lenses, have to be introduced into any desired path of rays.

Further advantageous embodiments and combinations of features of the invention emerge from the following detailed description and the patent claims as a whole.

BRIEF DESCRIPTION OF THE DRAWINGS

In the drawings used for explaining the exemplary embodiment:

FIG. 12 shows the lens holder from FIG. 11 with the current switched on and

In principle, the same parts are provided with the same designations in the figures.

Ways of Implementing the Invention

The invention is to be explained in detail below on the basis of several examples.

Figure 1:
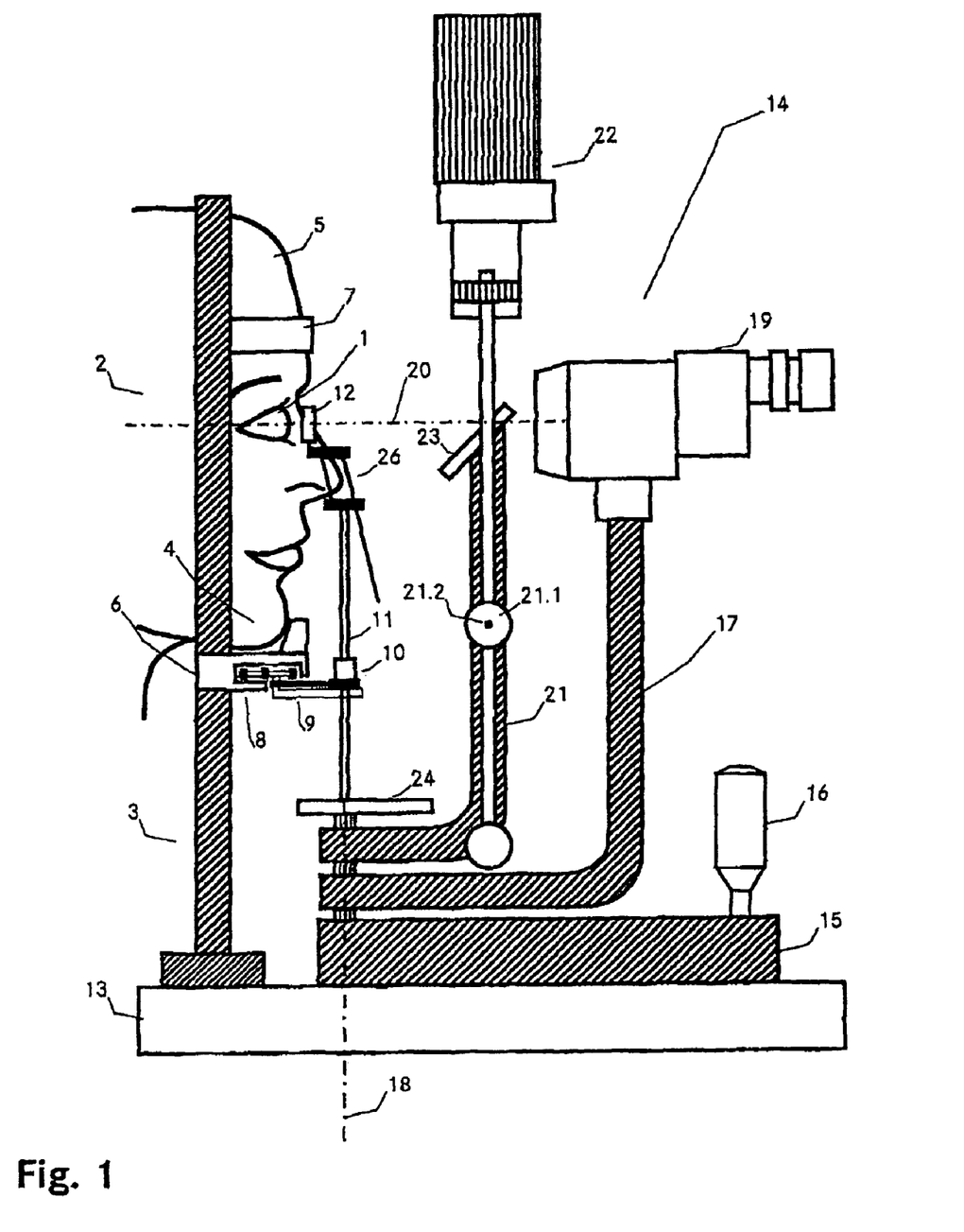
FIG. 1 shows a device according to the invention for forming an image of the eyeground.

FIG. 1 shows a slit lamp unit 14 according to the invention from the side, mounted on a table 13, for forming an image of the rear portions, in particular the fundus (eyeground), of the eye 1 of a patient 2. The head of the patient 2 is fixed in a head holder 3. For this purpose, the chin 4 and forehead 5 of the patient are resting on a chin support 6 and a forehead support 7, respectively.

The chin support 6 has a rail 8, which lies perpendicularly in relation to the image plane and in which a lens carriage 9 can be moved back and forth (perpendicularly in relation to the image plane). The lens carriage 9 comprises a shaft guide 10, into which there has been introduced a lens holder 11, which bears at its upper end a lens 12, as an auxiliary lens.

Mounted on the side of the head holder 3 opposite from the patient 2 there is a slit lamp unit 14. This comprises a cross slide 15 with a steering lever 16, with the aid of which the slit lamp unit 14 can be moved horizontally (for example by inclining the steering lever 16) and vertically (for example by turning the steering lever 16).

In conjunction with the slit lamp unit 14, the lens 12 on the lens holder 11 can be moved freely, and of course also positioned in front of the eye 1, by lateral displacement of the lens carriage 9 and by vertical displacement in the shaft guide 10.

Furthermore, a microscope 19, for example a Greenough stereo microscope with an optical axis 20, is fastened on a microscope arm 17, which can be pivoted about a vertically upright pivot axis 18 (here, the optical axis 20 refers to the center perpendicular of the optical axes of the optical subsystems on the left and on the right of the microscope 19).

Fastened to a lamp arm 21, which is likewise pivotable about the pivot axis 18, as a lighting unit is a slit lamp 22, the light of which is cast via a mirror 23 into the eye 1 to be examined. To reduce or eliminate disturbing reflections of light in the eye 1, the slit lamp 22 is fastened to the lamp arm 21 in such a way that it can be pivoted about the joint 21.1 with the pivot axis 21.2 which is perpendicular in relation to the image plane. The slit lamp 22 produces, for example, a light slit with which the eyeground is illuminated. The entire image field can be scanned by displacing the slit lamp unit laterally and/or vertically. In addition to the slit lamp 22, a further light source, for example the output of a light guide, may be provided, for example on a movable arm, serving for example for lighting up the entire eyeground, while only a narrow strip of the fundus is brightly lit up by the light slit produced by the slit lamp 22.

The device further comprises a guide plate 24, which is likewise pivotable about the pivot axis 18 and is coupled to the microscope arm 17, so that it follows the pivoting movements of the latter.

On the upper side of the guide plate 24 there is a guide groove 24.1 (which is not visible in FIG. 1). As a result of the rotary coupling of the guide plate 24 to the microscope arm 17, this guide groove 24.1 always runs parallel to the optical axis 20 of the microscope 19.

Inserted into this guide groove 24.1 is the lower end of the lens holder 11, which has been introduced into the shaft guide 10.

In this way, the lens 12 is coupled in terms of movement to the microscope 19 at the upper end of the lens holder 11. When there are lateral movements (horizontally, perpendicularly in relation to the optical axis 20) and vertical movements of the microscope 19, the lens 12 is made to follow the movement via the guide plate 24 and lens holder 11. When there are movements forward or back in the direction of the optical axis 20, the lens holder 11 slides forward and back in the guide groove 24.1, without the distance of the lens 12 from the eye 1 changing. To be able to set this distance, the lens 12 is connected to the lens holder, for example, by means of a parallel joint 26.

Figure 13:
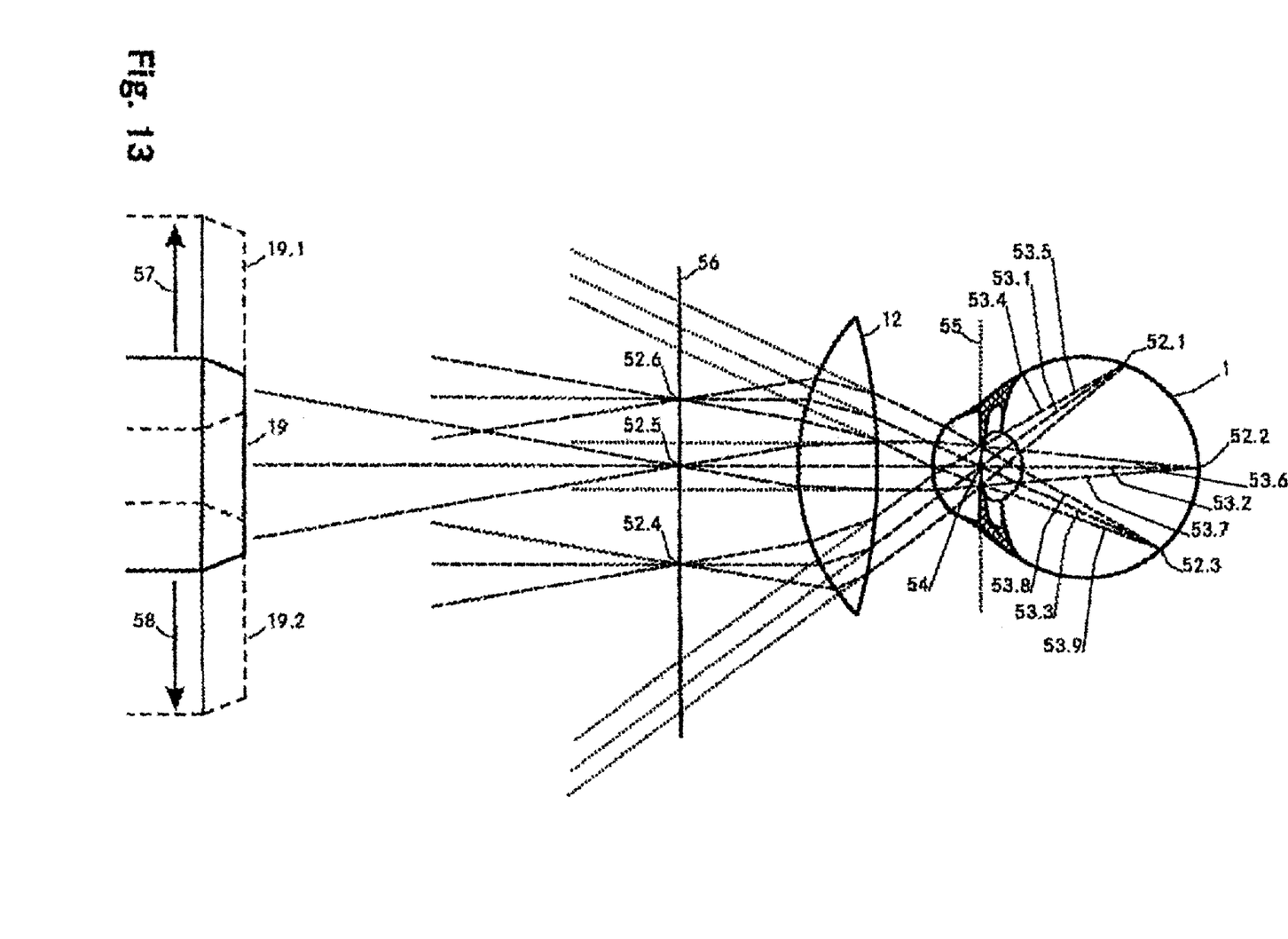
FIG. 13 shows several paths of rays for forming an image of the fundus.

When forming the image of the eyeground, the lens 12 consequently lies exactly in the optical axis 20 between the eye 1 and the microscope 19. As already mentioned, the lens 12 makes it possible to view a large area of the fundus of the eye with the microscope 19, which is illustrated in FIG. 13. For the sake of simplicity, only the path of rays for three points of the fundus 52.1, 52.2, 52.3 of the eye 1 is represented in FIG. 13. Respectively represented for each point of the fundus 52.1, 52.2, 52.3 are the principal ray 53.1, 53.2 and 53.3 and the two marginal rays 53.4, 53.5, 53.6, 53.7, 53.8 and 53.9, which just still pass through the pupil of the eye 1 to the outside. The principal rays 53.1–53.3 and the marginal rays 53.4–53.9 are refracted at the cornea, i.e. the interface between the eye 1 and the air. All the rays originating from a single point of the fundus of the eye 1 run parallel outside the eye 1 (assuming a healthy eye 1). The refraction of the rays at the crystalline lens is negligible in comparison with the refraction at the cornea and is therefore not shown. If the lens 12 were not present, these rays 53.1–53.9 would continue to run in a straight line (represented as dotted lines).

An image is formed by the lens 12 of all the rays of a single point of the fundus 52.1–52.3 onto an image plane 56, so that an image 52.4–52.6 is produced. The distance between the lens 12 and the plane of the pupil 55 corresponds approximately to the focal length of the lens 12. In this way, the telecentric condition is satisfied and the principal rays 53.1, 53.2, 53.3 are all parallel to the optical axis 20 in the direction of the microscope 19.

To be able to view this image in the image plane 56 with the microscope 19, the microscope 19 just has to be focused to the image plane 56. To be able to view or scan all the regions of the fundus, the microscope 19 is displaced in a plane parallel to the image plane 56, without changing the distance of the microscope 19 from the image plane 56 or from the eye 1. This displacement is represented by the two arrows 57 and 58. Two different positions of the displaced microscope 19.1 and 19.2 are depicted by dashed lines. This easy method of setting is only possible if the distance between the lens 12 and the plane of the pupil 55 is chosen such that the telecentric condition is satisfied.

Furthermore, this displacement allows the greatest possible luminous flux from the region of the fundus which is to be viewed to be captured, i.e. the brightest possible image of the region of the fundus which is to be viewed to be obtained.

To make it easier for the viewer to displace the microscope 19 parallel to the image plane 56, the cross slide 15 could be provided, for example, with a kind of brake, which could be switched on after the positioning of the lens 12 and the microscope 19. This brake would then provide an increased movement resistance of the cross slide 15 in the direction toward the eye 1 (or away from it) or make such microscope displacements completely impossible. However, blocking of the cross slide 15 is not very advantageous, since, even with such accurate positioning, small corrections of the distance of the microscope are sometimes necessary.

Positive lenses 12, which produce an actual image of the fundus of the eye between the lens 12 and the microscope, are preferably used, although negative lenses 12, which produce a virtual image (behind the lens 12 as seen from the microscope), can also be used.

Figures 2, 3, 4:
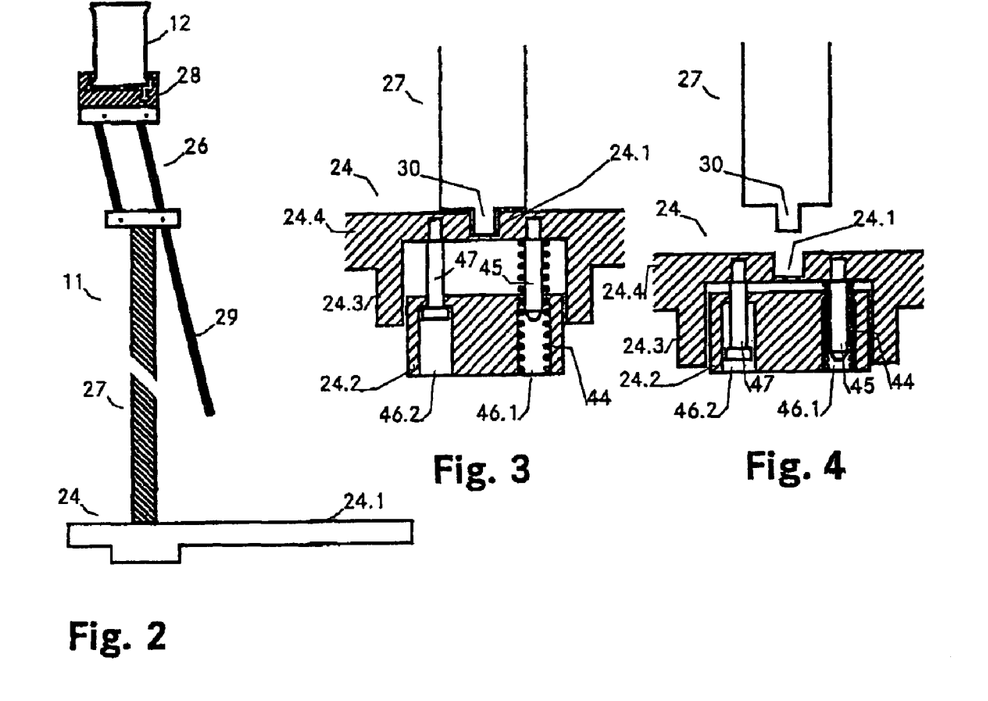
FIG. 2 shows a lens holder with a lens, mounted on the guide plate.
FIG. 3 shows a cross section through the guide plate with the lens holder.
FIG. 4 shows the cross section from FIG. 3 with the guide plate pressed together.

FIG. 2 shows the lens holder 11 and the guide plate 24 on a larger scale. The lens holder 11 comprises a shaft 27 and, at the upper end of the latter, the parallel joint 26. This comprises a linkage which is formed in the manner of a parallelogram and the sides of which are connected to one another in a jointed manner. One side of the parallelogram is perpendicular in relation to the shaft 27 and is firmly connected to the upper end of the latter. Connected to the side parallel to the latter side is a clamping device 28, into which the lens 12 can be firmly clamped on the lens holder 11 and removed again manually in an easy manner. This is particularly helpful if the lens 12 is to be exchanged for another lens during the examination. For changing the distance of the lens 12 from the eye 1, one of the other two sides is lengthened and forms an adjusting lever 29.

In FIGS. 3 and 4, a longitudinal section through the lower end of the shaft 27 and the guide plate 24 is represented. Formed at the lower end of the shaft 27 is an adjusting spring 30, which is fitted in a guide groove 24.1 of the guide plate 24. The adjusting spring 30 extends over the entire width of the shaft 27 and lies parallel to the optical axis of a lens 12 mounted on the lens holder 11.

The guide plate 24 comprises a lower part 24.2 and an upper part, which comprises a plate 24.4 with the guide groove 24.1 and a kind of hollow cylinder 24.3, which is attached on the underside of the plate 24.4. The outside diameter of the lower part 24.2 is smaller than the inside diameter of the hollow cylinder 24.3. Both are formed in such a way that the lower part 24.2 can be pushed into the hollow cylinder 24.3 from below.

A helical spring 44 is fastened between the upper part and the lower part 24.2 in such a way that the parts pushed one into the other are pressed apart. In order that the two parts do not cant when they are pushed one into the other or pushed apart, fitted inside the hollow cylinder 24.3 is a guide pin 45, which is guided in a guide bore 46.1 on the lower part 24.2. The guide bore 46.1 is used at the same time for guiding the helical spring 44. In order that the upper part and lower part 24.2 are not pressed too far apart by the helical spring 44, provided in the lower part 24.2 is a further guide bore 46.2, through which a screw 47 is screwed from below into the plate 24.4 of the upper part. The head of the screw 47 serves as a stop, in order that the hollow cylinder 24.3 and the lower part 24.2 do not fall apart. The screw also serves at the same time for improving the guidance of the lower part 25.2 in the hollow cylinder 24.3.

The upper part has on its upper side a guide groove 24.1, into which the adjusting spring 30 of the shaft 27 can be fitted. The guide groove 24.1 extends continuously over the entire length of the guide plate 24, so that the shaft 27 inserted into the guide groove 24.1 is horizontally movable in the direction of the guide groove 24.1. As already mentioned, the guide plate 24 itself is connected to the microscope arm 17 pivotably about the pivot axis 18, so that it follows a pivoting movement of the microscope arm 17.

FIG. 3 shows the cross section through the guide plate 24 in the pressed-apart state, i.e. with the helical spring 44 relaxed (more or less) and the shaft 27 of the lens holder 11 inserted. FIG. 4, on the other hand, shows the guide plate 24 in the pressed-together state. The helical spring 44 is compressed and the shaft 27 (fixed in the guide 10 on the lens carriage 9) is no longer inserted in the guide groove 24.1. By pressing together, the shaft 27 is released and the lens holder 11 or the lens 12 is consequently uncoupled in terms of movement from the guide plate 24 and from the microscope 19.

By means of a fixing mechanism which is not represented, the guide plate engages, for example in the pressed-down position, and releases the adjusting spring 30 of the lens holder 11 (in a way similar to when a refill of a ballpoint pen is fixed in the writing position or transporting position). After that, the desired examinations can be carried out, it being possible for the guide plate 24 also to be removed completely beforehand to increase the freedom of movement of the slit lamp unit. By replacing the guide plate 24 and pressing it once again, the arrestment is released, for example, and the guide plate is back in the original position.

Figure 5:
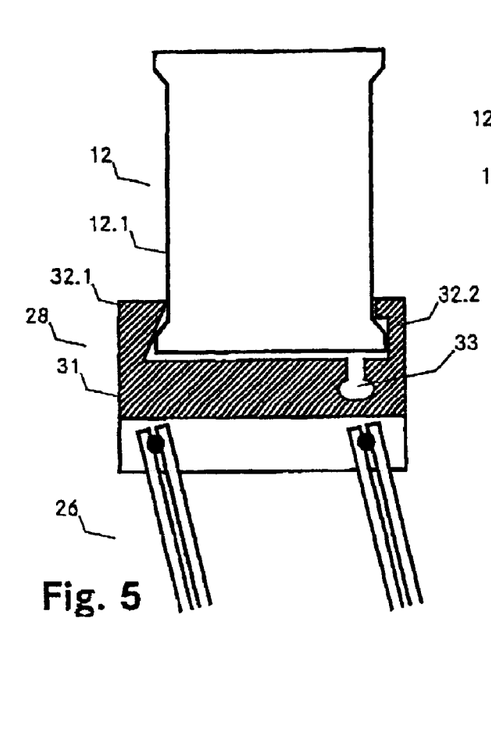
FIG. 5 shows a lateral view of a detail of the upper end of the lens holder.
Figure 6:
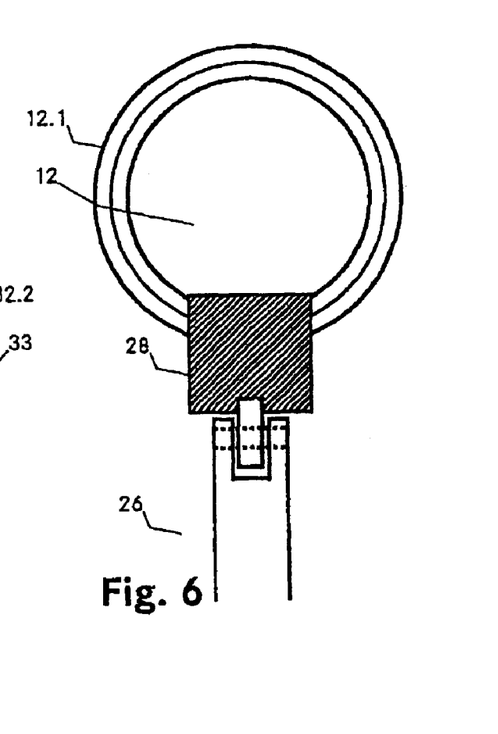
FIG. 6 shows a front view of the upper end of the lens holder.

FIGS. 5 and 6 show a cross section and a frontal view of the clamping device 28 with a mounted lens 12, which is held in a lens mount 12.1 and fastened to the parallel joint 26. The clamping device 28 comprises a base 31 and also a front holding part 32.1 and a rear holding part 32.2, which are fastened at a specific distance from each other on the base 31. The distance between the two holding parts 32.1 and 32.2 on the base 31 is either fixed by being made to match the thickness of a specific lens or the width of the lens mount or can be variably set. Moreover, the two holding parts 32.1 and 32.2 are formed in such a way that the distance between them become smaller as the vertical distance from the base 31 increases.

The base 31 and/or the holding parts 32.1 and 32.2 consist of an elastic material, in order that a lens 12 which has a lens mount 12.1 which is wider than the smallest distance between the two holding parts 32.1 and 32.2 can be clamped between the latter.

To increase the spring action of the holding parts 32.1 and 32.2, a slot 33 is formed in the base 31.

Figure 7:
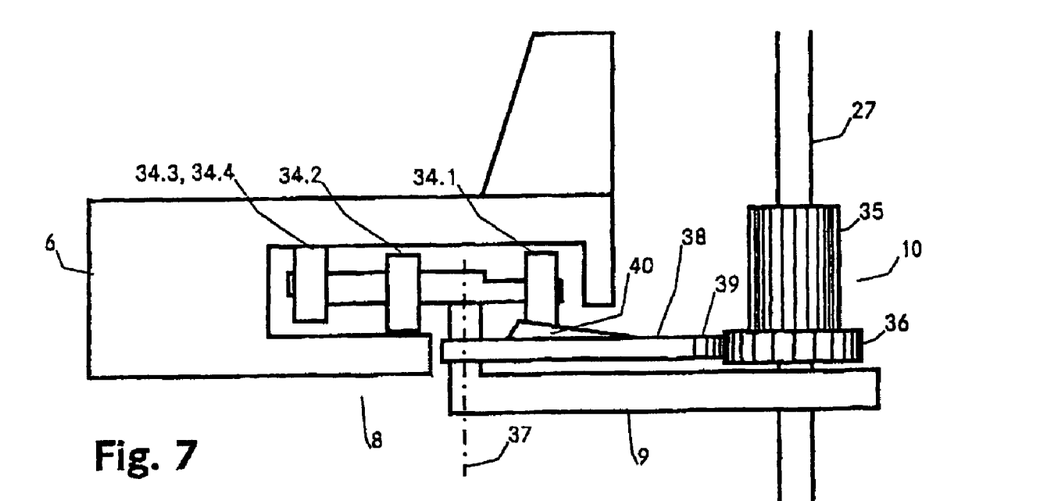
FIG. 7 shows a lens carriage with a lens holder guide.

In FIG. 7, the chin support 6 with the lens carriage 9 running in the rail 8 is represented from a lateral view. The lens carriage 9 runs on a plurality of roller 34.1, 34.2, 34.3, and 34.4. The shaft guide 10 on the lens carriage 9 comprises a knurled screw 35 (which may also be configured just as a sleeve), which has a ring of teeth 36 at its lower end. By turning the knurled screw 35, the shaft 27 of a lens holder introduced into the shaft guide 10 is firmly clamped in the shaft guide 10. This takes place, for example, in a known manner by means of reducing the inside diameter of the shaft guide 10.

Also provided on the lens carriage 9 is an eccentric 38, which is pivotably mounted about a pivot axis 37 and has a further ring of teeth 39, which is not completely formed and the teeth of which engage in the ring of teeth 36 of the shaft guide 10. By turning the knurled screw 35, consequently not only is the shaft 27 firmly clamped but the eccentric 28 is also additionally turned about the pivot axis 37. On the eccentric 38 there is an elevation 40, which is made by the turning of the eccentric 38 to come to lie under the roller 34.1 and block the latter, for example by pressing it against the rail 8. As a result, the movement of the lens carriage 9 in the rail 8 is braked or completely blocked.

A further possible way of blocking the lens carriage 9 in the rail is that an outer edge of the eccentric 38 is formed in such a way that its pivoting has the effect that it is pressed against the rail 8.

Figure 8:
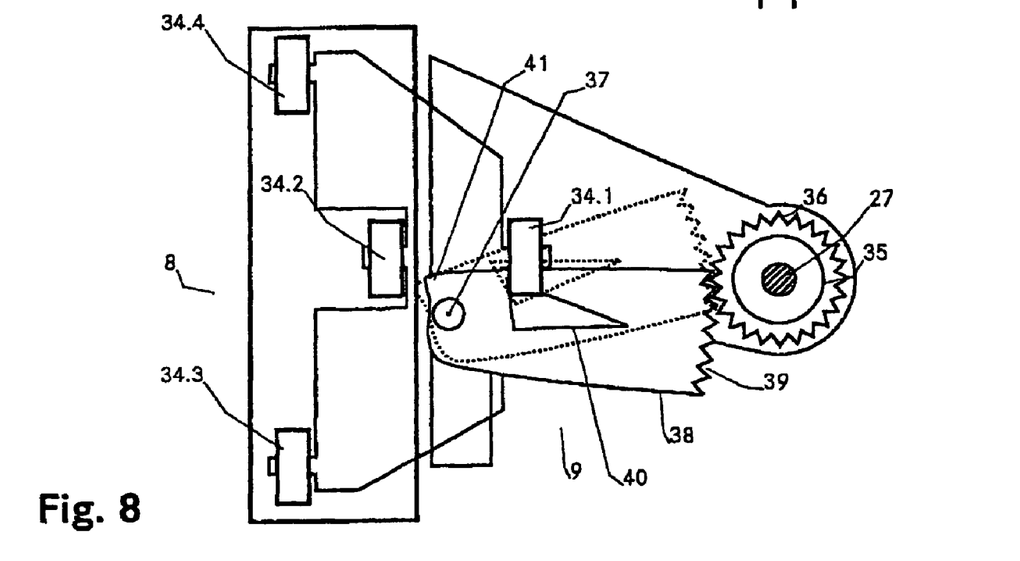
FIG. 8 shows a view of a detail of the lens carriage from above.

In FIG. 8, which shows the lens carriage 9 (at least partly), seen from above, with the shaft guide 10 and part of the rail 8, a special form with a bulge 41 of the eccentric 38 is represented by way of example. In the non-blocking position (solid lines), the bulge 41 is located at a specific distance from the rail 8, so that the lens carriage 9 can be displaced laterally in any way desired. If the knurled screw 35 is turned clockwise, the bulge 41 moves closer to the rail 8, until it finally touches it and is pressed against it (dotted lines). The lens carriage is blocked as a result.

Figure 9:
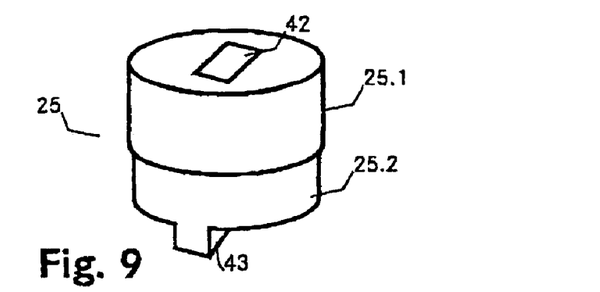
FIG. 9 shows an adapter for coupling the lens holder to the slit lamp unit.

Instead of forming the guide plate 24 in such a way that it can be moved out of the shaft 27 by pressing together, an adapter 25, as shown in FIG. 9 in a perspective representation, may also be used. The adapter comprises an upper part 25.1, a kind of hollow cylinder with a cover, and a lower part 25.2, the outside diameter of which is smaller than the inside diameter of the upper part 25.1. Both are formed in such a way that the lower part 25.2 can be pushed into the upper part 25.1 from below. The upper part 25.1 in this case corresponds to the hollow cylinder 24.3 and the lower part 25.2 corresponds to the lower part 24.2 of the guide plate 24 from FIGS. 3 and 4. The upper part 25.1 has on its upper side a groove 24, into which the adjusting spring 30 of the shaft 27 can be fitted. However, the groove 42 is not continuous, so that the shaft 27 inserted into the adapter 25 is completely fixed horizontally. The lower part 25.2 of the adapter 25 has on its underside an adjusting spring 43 fitting exactly into the guide groove 24.1 of the guide plate 24.

In the adapter 25 there is the same mechanism as FIGS. 3 and 4 show for the guide plate 24. This form of the adapter 25 allows it to be inserted with its adjusting spring 43 into the guide groove 24.1 of the guide plate 24 and the adjusting spring 30 of the shaft 27 of a lens holder 11 which has been introduced into the shaft guide 10 to be inserted into the groove 42 of the adapter 25. In this way, the lens 12 fastened to the lens holder 11 is coupled in terms of movement to the microscope 19.

For fixing the lens holder 11 after positioning in front of the eye 1 of the patient 2, the knurled screw 35 is turned clockwise. As a result, on the one hand the lens holder 11 is firmly clamped in the shaft guide 10 and, via eccentric 38, on the other hand the lens carriage 9 is firmly clamped in the rail 8 of the chin support 6.

The uncoupling of the lens holder 11, and consequently of the lens 12, from the microscope 19 while retaining the spatial fixing is performed by pressing the upper part 25.1 of the adapter 25 downward. As a result, the adjusting spring 30 of the lens holder 11, which had previously been inserted in the groove 42 of the upper part 25.1, is released (see also FIG. 4). After that, the adapter 25 itself can be removed from the guide plate 24 by horizontal displacement in the guide groove 24.1. (An arrestment in the pressed-together position is not absolutely necessary in this example.)

Figure 10:
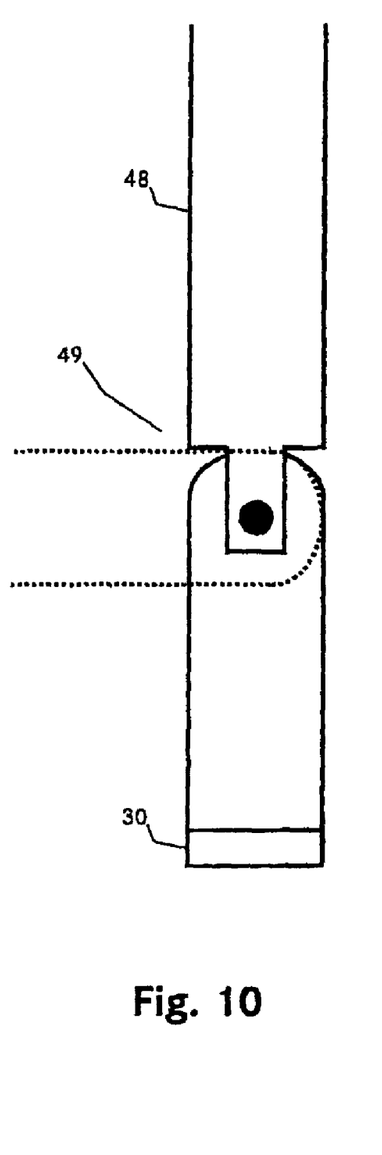
FIG. 10 shows a lateral view of a detail of the lower end of the lens holder with a buckling joint.

FIG. 10 shows a further example of the shaft 48 of a lens holder 11. The lower end of the shaft 48 with the adjusting spring 30 is connected to the rest of the shaft 48 by means of a buckling joint 49. The buckling joint 49 is formed such that it can be arrested both in the extended position (solid lines) and in the bent-around position (dotted lines). The bending around of the end of the shaft is performed in the longitudinal direction of the adjusting spring 30, i.e. the pivot axis of the buckling joint is perpendicular to the image plane. This allows the spatially fixed lens holder 11 to be uncoupled in terms of movement from the microscope 19 by simply bending around the lower end of the shaft.

It goes without saying that it is also possible to realize not only the uncoupling but also the spatial fixing of the lens holder 11 by bending around the end of the shaft. For example, when the lower end of the shaft 48 is bent around, the knurled screw could be turned by means of a lever mechanism located in the interior of the shaft 48, or a mechanism for fixing the lens holder 11 in the shaft guide 10 and also for fixing the lens carriage 9 in the rail 8 is actuated directly.

Figure 11:
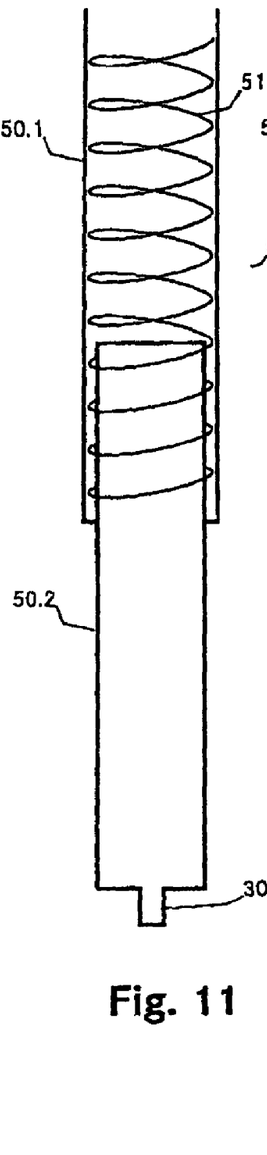
FIG. 11 shows a view of a detail of an electromagnetically operating, telescopically formed lower end of the lens holder with the current switched off.
Figure 12:
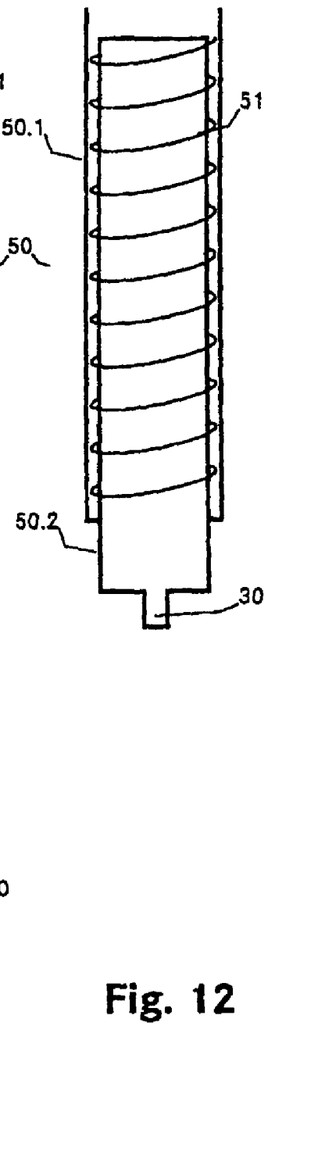

FIGS. 11 and 12 show a further example of the configuration of the shaft 50 of the lens holder 11. The shaft 50 is of a two-part configuration. It comprises an upper part 50.1, formed as a hollow cylinder, and a cylindrically formed lower part 50.2, the outside diameter of the lower part 50.2 being smaller than the inside diameter of the upper part 50.1. The lower part 50.2 is produced from magnetizable material and has in turn at its lower end the adjusting spring 30. On the inner side of the upper part 50.1, an electrical conductor is wound up spirally to form a coil 51, the ends of which are connected in an electrically conducting manner to an electrical power supply (not represented). The power supply comprises, for example, a battery in the upper part 50.1 of the shaft 50. The supplying of the power may also take place from an external power supply, for example via guide plate 24, via lens carriage 9 or via freely routed cables.

If, for example, by pressing a button, a constant electric voltage is applied to the ends of the conductor of the coil 51, a magnetic field is generated in the interior of the coil 51, pulling the lower part 50.2 of the shaft 50 into the coil 51 and consequently pulling it upward.

It goes without saying that fixing of the lower part 50.2 in the pulled-in and/or moved-out position may also be provided. Or the lower part 50.2 is formed as a magnet, for example as a bar magnet, and is pulled upward or pressed downward by switching on the current. Furthermore, there may also be tension springs or compression springs, which move the lower part 50.2 back into the original position again after deflection by the magnetic field.

Here, too, the fixing of the shaft 50 in the shaft guide 10 and/or of the lens carriage 9 in the rail 8 may be performed in various ways: either mechanically in the way already presented, by the knurled screw being turned by the pulled-up lower part 50.2 of the shaft, or likewise magnetically, by for example a movably mounted part of the lens carriage 9 being pulled toward the lens holder 11 by the generated magnetic field and the lens holder and lens carriage fixed in this way.

A further kind of magnetic fixing is performed for example by a magnet being introduced into a magnetic circuit by the bending around of the lower end of the shaft 48 from FIG. 10 and said circuit being closed as a result. The magnetic circuit runs, for example, from the lens holder 11 via the shaft guide 10 and lens carriage 9 to the rail 8 and back again to the lens holder 11. The fixing could be performed, for example, by exploiting the fact that, after the closing of the magnetic circuit, the magnetic forces attempt to reduce the magnetic resistance, in that moving parts of the magnetic circuit are minimally displaced (i.e. the corresponding air gaps are reduced) and in this way firmly clamp the lens holder and the lens carriage.

To sum up, it can be stated that the device according to the invention allows an image of the rear portions of an eye to be formed in an optimum way, in that the auxiliary lens which is necessary for the image formation can be positioned with the aid of the microscope very precisely in front of the eye to be examined, and spatially fixed thereafter in an easy way, and can be uncoupled from the microscope in the same working step. The examination is subsequently performed with the freely movable microscope.

The invention claimed is:

1. A method for forming an image of a rear portion of a patient's eye with a viewing unit and an optical unit comprising at least the following steps:
   a) the optical unit is coupled in terms of movement to the viewing unit,
   b) the optical unit is positioned in front of the patient's eye in such a way that it is located between the viewing unit and the patient's eye in a given relative position with respect to the patient's eye,
   c) the optical unit is spatially fixed in relation to the patient's eye,
   d) the optical unit is uncoupled from the viewing unit while maintaining the spatial fixing in relation to the patient's eye,
   e) by moving the viewing unit, the rear portion of the patient's eye is viewed or an image of it is formed.

2. The method according to claim 1, wherein the optical unit is positioned in front of the patient's eye in such a way that a focus of the optical unit comes to lie on a plane of the pupil of the patient's eye.

3. The method according to claim 1 or 2, wherein the spatial fixing and the uncoupling of the optical unit are substantially at the same time.

4. A device with a viewing unit and an optical unit for forming an image of a rear portion of a patient's eye, comprising means for coupling the optical unit in terms of movement to the viewing unit, means for positioning the optical unit coupled to the viewing unit between the viewing unit and the patient's eye, means for spatially fixing the optical unit in relation to the patient's eye and also means for uncoupling the spatially fixed optical unit from the viewing unit.

5. The device according to claim 4, wherein the viewing unit is a microscope and the optical unit is an auxiliary lens.

6. The device according to claim 4 or 5, further comprising a head holder for the locational fixing of a patient's head and consequently of the patient's eye, and the means for coupling the optical unit to the viewing unit further comprise a lens carriage, which is fastened to the head holder in a horizontally movable manner, a lens holder with a shaft and also a guide plate, which is fixedly assigned locationally to the viewing unit and has a guide groove, the optical unit being fastened to the lens holder and the shaft being able to be introduced into a corresponding shaft guide on the lens carriage and positioned in relation to the fixed patient's eye, and the optical unit being able to be coupled in terms of movement to the viewing unit by inserting the lower end of the shaft which has been introduced into the shaft guide on the lens carriage into the guide groove, it being possible for the shaft to be inserted into the guide groove securely to prevent twisting, directly or by means of an adapter.

7. The device according to claim 6, wherein the lens holder can be spatially fixed in the shaft guide on the lens carriage and/or the lens carriage can be spatially fixed on the head holder mechanically or magnetically.

8. The device according to claim 7, wherein the shaft guide on the lens carriage has a sleeve with a ring of external teeth, it being possible by turning of the sleeve for a clamping mechanism for firmly clamping the shaft in the sleeve to be actuated and/or for a brake for firmly clamping the lens carriage on the head holder to be activated via the ring of external teeth.

9. The device according to claim 6, wherein the lens holder, the guide plate and the adapter, if provided, are formed in such a way that the spatially fixed optical unit can be uncoupled in terms of movement from the viewing unit by horizontal and/or vertical moving out or pivoting out of the lower end of the shaft, of the guide plate or of the adapter.

10. The device according to claim 4, wherein said device is formed in such a way that the optical unit can be uncoupled from the viewing unit and spatially fixed in relation to the patient's eye substantially at the same time and without any locational displacement.

11. The device according to claim 4, wherein an image acquisition device, for recording images of the rear portion of an eye can be connected to the viewing unit.

12. The device according to claim 4, further comprising a lens holder, wherein the optical unit can be mounted on the lens holder and removed again manually.

13. The device according to claim 12, wherein the lens holder has two holding parts resiliently connected to each other, between which the optical unit can be clamped.

* * * * *